United States Patent [19]

Roberfroid et al.

[11] Patent Number: 4,673,690

[45] Date of Patent: Jun. 16, 1987

[54] ACYLATED ENAMIDES AND PHARMACEUTICAL COMPOSITIONS CONTAINING THEM

[75] Inventors: Marcel B. Roberfroid, Louvain-La-Neuve; Heinz G. Viehe, Limal; Françoise M. Hervens, Sint-Agatha-Rode, all of Belgium

[73] Assignee: Biotec, Belgium

[21] Appl. No.: 644,719

[22] PCT Filed: Dec. 20, 1983

[86] PCT No.: PCT/BE83/00022

§ 371 Date: Aug. 23, 1984

§ 102(e) Date: Aug. 23, 1984

[87] PCT Pub. No.: WO84/02523

PCT Pub. Date: Jul. 5, 1984

[30] Foreign Application Priority Data

Dec. 27, 1982 [FR] France ............................ 82 21965

[51] Int. Cl.$^4$ .......................................... A61K 31/195
[52] U.S. Cl. ...................... 514/563; 562/426; 562/440; 562/444; 562/449; 562/429; 562/450; 514/492; 514/562
[58] Field of Search ............ 562/426, 449, 440, 450, 562/575, 444; 560/41; 424/319; 260/429; 514/562, 563, 492

[56] References Cited

U.S. PATENT DOCUMENTS

| | | | |
|---|---|---|---|
| 2,449,191 | 9/1948 | Behrens | 562/450 |
| 2,483,530 | 10/1949 | Clark | 562/444 |
| 3,402,198 | 9/1968 | Bolhofer | 562/426 |
| 4,421,765 | 12/1983 | Sallmann et al. | 562/450 |

FOREIGN PATENT DOCUMENTS 1273862 9/1961 France ............................ 562/450

OTHER PUBLICATIONS

Gallina et al., J.C.S. Perk Tran 1, 1973, pp. 1134–1136 (1973).

Wieland et al., Chem. Ber., vol. 90, pp. 194–201 (1957).
Rzeszolarska et al., Chem. Abst., vol. 100, #519, 76p (1983).
Rho et al., Chem. Abst., vol. 79, #5552y (1973).

*Primary Examiner*—James H. Reamer
*Attorney, Agent, or Firm*—Fishman & Dionne

[57] ABSTRACT

The acylated enamide compounds are acylated enamides corresponding to the general formula

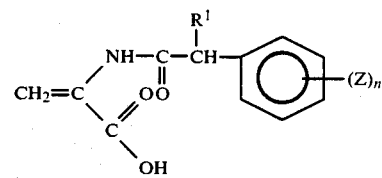

in which
Z represents an electron donor group,
n is 1, 2 or 3, and
$R^1$ represents hydrogen, a halogen or any organic group,
or salts, complexes, alkylated derivatives or acylated derivatives of these compounds.

Typical acylated enamide compounds according to the invention correspond to the formula

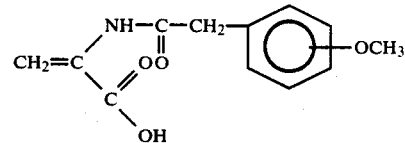

These acylated enamide compounds and the pharmaceutical compositions containing the compounds are useful in the prevention and treatment of cancers.

11 Claims, No Drawings

ACYLATED ENAMIDES AND PHARMACEUTICAL COMPOSITIONS CONTAINING THEM

The present invention relates to acylated enamide compounds consisting of acylated enamides as well as their salts, their complexes and their acylated and alkylated derivatives. The invention also relates to pharmaceutical compositions which contain these compounds and which can in particular be used for the prevention or treatment of cancers, the use of these compounds for the prevention of cancers and a process for the preparation of these compounds.

The acylated enamide compounds according to the invention are compounds corresponding to the general formula:

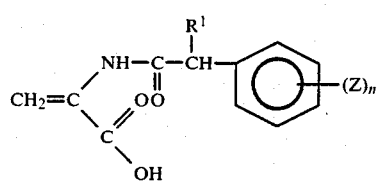 (I)

in which
Z represents an electron donor group,
n is 1, 2 or 3, and
$R^1$ represents hydrogen, a halogen or any organic group,
or salts, complexes, alkylated derivatives of acylated derivatives of these compounds.

The salts of these compounds can for example be ammonium salts, alkali metal salts such as the sodium or potassium salt, alkaline earth metal salts such as the magnesium and calcium salts, and salts of organic bases. The complexes of these compounds can be those formed with, for example, any metal salts. By acylated derivatives of these compounds, there are understood derivatives such as the esters and the amides of these compounds; preferably, the aromatic nucleus carrying the group Z does not contain acylated substituents.

Usually, the donor group is a halogen or a group selected from amongst the groups $OR^2$, $SR^2$, $SeR^2$, $N=R^2$ or $NR^2R^3$, in which the oxygen, sulphur, selenium and nitrogen can form part of a ring and $R^2$ and $R^3$ can be identical or different and represent hydrogen or a saturated or unsaturated aliphatic or cyclic organic group containing from 1 to 20 carbon atoms. Most commonly, $R^2$ and $R^3$ represent a substituted or unsubstituted alkyl group containing from 1 to 6 carbon atoms. Preferably, the donor group is an $OR^2$ group, where $R^2$ represents hydrogen or a substituted or unsubstituted alkyl group containing from 1 to 6 carbon atoms. A very particularly preferred donor group is a methoxy group $-OCH_3$.

Usually, $R^1$ represents hydrogen, a halogen or any organic group. Preferably, $R^1$ represents hydrogen or a substituted or unsubstituted aliphatic group containing from 1 to 4 carbon atoms, or an aromatic group containing from 5 to 8 carbon atoms. A particularly preferred meaning of $R^1$ is hydrogen.

The preferred acylated enamide compounds according to the invention are the (methoxyphenylacetyl)-dehydroalanines of the formula

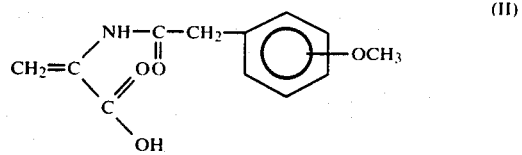 (II)

Amongst these, the preferred acylated enamide compound is that in which the methoxy substituent is in the paraposition.

A process for the preparation of acylated enamide compounds according to the invention consists of reacting an amide of the formula

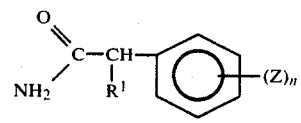

where $R^1$, Z and n are as defined above, with pyruvic acid. The reaction can be carried out by bringing 1 mol of amide together with 1.2 mols of freshly distilled pyruvic acid and heating these, in benzene, to the reflux temperature in an apparatus equipped with a water separator. Refluxing is stopped when water ceases to separate out. The mixture is left until a precipitate forms and is then filtered, and the precipitate is treated with a saturated $NaHCO_3$ solution. The fraction which is insoluble in a basic medium and which consists of unreacted amide is separated off and concentrated hydrochloric acid is then added gradually to the filtrate until a pH of about 3.5 and a precipitate result. After filtration and recrystallisation from ethanol, yields of between 30% and 95% are obtained. It can happen that a precipitate is not obtained after refluxing in benzene solution; in that case, the benzene is evaporated and the residue is treated in the same manner as described above.

The acylated enamide compounds according to the invention can also be prepared by any other appropriate organic synthesis. For example, the process described in French Pat. No. B-2,349,567 (SUMITOMO CHEMICAL COMPANY) can be employed.

The acylated enamide compounds according to the invention can be used as medicaments and especially for the treatment, in human or veterinary medicine, of all malignant tumoral proliferations such as cancers of various origins, regardless of the age and histological type of the tissue at the expense of which these cancers have formed. The compounds can also be used for the prevention of these same diseases, for example by using the compounds as a food additive.

The invention also relates to the parmaceutical compositions containing as the active ingredient an acylated enamide compound as defined above. These compounds can furthermore contain an antineoplastic substance for simultaneous, separate or long-term use in cytostatic therapy. The known antineoplastic substances generally suffer from the serous disadvantage of having a high degree of toxicity which causes particularly harmful secondary effects such as damage to the normal tissues. The pharmaceutical compositions according to the invention have both a reduced degree of toxicity and an improved therapeutic effect compared to the known compositions containing only antineoplastic substances.

By an antineoplastic substance there is meant any substance which can be used for the purpose of destroying the cancer cells or preventing their appearance and proliferation. Compounds of very diverse chemical nature are known to be antineoplastic substances; they include alkylating agents such as cyclophosphamide, melphalan, chlorambucil, chlormetine and other nitrogen mustards, ethyleneimines, an example being thiothepa, sulphonic esters including busulfan, antimetabolites such as methotrexate and other anti-folic acid compounds, mercaptopurine and other anti-purine compounds, fluorouracil, cytarabine and other anti-pyrimidine compounds, azaserine, hormonal modifiers such as the androgens, the oestrogens, the progestational agents and the glucocorticoids, enzymes such as asparaginase, antibiotics such as bleomycin, dactinomycin, daunorubicin, meractinomycin, mitomycin, rufocromycin, methramycin, doxorubicin (sometimes called adriamycin), plant extracts such as alkaloids from the periwinkle and the colchicum and other fusorial poisons, radioactive isotopes such as sodium radiophosphate, sodium radioiodide or other compounds such as methylglyoxal bis(guanylhydrazone), derivatives of podophyllotoxin, mitotane, pipobromane, nitrosoureas and hydroxyurea. The antineoplastic substances preferably present in the pharmaceutical compositions according to the invention are the nitrogen mustards, the antibiotics and anti-pyrimidine compounds and very especially cyclophosphamide, daunorubicin, doxorubicin and fluorouracil.

The pharmaceutical compositions according to the invention can be used for the treatment and prevention in human medicine or veterinary medicine, of all malignant tumoral proliferations such as cancers.

The pharmaceutical compositions according to the invention can also contain other active substances which can be used in pharmaceutical compositions for the prevention or treatment of cancers, and especially ascorbic acid.

Of course they also contain formulating additives which allow the compositions to be administered conveniently, to example in the form of powders, tablets, ointments, lotions, capsules, coated tablets, pills, ampoules, syrups, emulsions, suppositories, injections or solutions. These additives can be suitable solid or liquid, organic or inorganic vehicles or pharmaceutical assistants, such as water, organic solvents of the paraffin type, gelatine, lactose, starch, magnesium stearate, talc, vegetable and animal fats and oils, gum, polyalkylene glycols or binders and other conventional assistants.

The pharmaceutical compositions according to the invention in general contain between 10% and 99% by weight of acylated enamide compounds according to the invention and, optionally, an antineoplastic substance. The weight ratio of the amounts of antineoplastic substance to acylated enamide compounds according to the invention present in the compositions according to the invention is in general between 1/10 and 10/1 and preferably between 1/4 and 4/1.

The acylated enamide compounds and the pharmaceutical compositions according to the invention can be administered for the treatment or prevention of malignant tumoral proliferations such as cancers in all mammals, but in particular in human patients, the administration being in the form of one or more "dosage units", in a pharmaceutically effective amount.

All methods of administration may be used, such as oral, rectal or parenteral administration as well as administration by epidermal application of various types of ointments or epidermal patches. By parenteral administration there are understood intravenous and intramuscular injections, as well as perfusion.

The pharmaceutical compositions according to the invention can be administered orally in human medicine in dosage units which in general contain at least 0.05 mg and up to 500 mg, preferably from 0.5 mg to 50 mg, of acrylated enamide compounds according to the invention and, optionally, an antineoplastic substance, together with a non-toxic pharmaceutically acceptable vehicle. Optionally, the pharmaceutical compositions according to the invention and the antineoplastic substances can be administered separately and at different times; in that case it is preferred to administer the pharmaceutical compositions according to the invention before administering the antineoplastic substances, the latter being administered after from 1 hour to 24 hours.

By "dosage unit" there is understood a unit dose which can be administered to a patient and can easily be handled and packaged so as to remain in the form of a physically stable unit dose containing the active ingredient either alone or mixed with solid or liquid pharmaceutical diluents or vehicles.

In the form of dosage units, the pharmaceutical compositions according to the invention can be administered once or several times daily at appropriate intervals, but at a [1 times taking account of the condition of the patient and the physician's prescriptions. The appropriate daily dose of the compositions according to the invention in general varies from 0.01 mg to 50 mg per kg of body weight.

For parenteral administration, especially for intravenous or intramuscular injections, the compositions according to the invention are for example administered in aqueous solution or suspension, in the form of a dosa unit containing from 0.5 mg to 50 mg of acylated enamide compound according to the invention, optionally together with an antineoplastic substance, the dosage unit being dissolved or suspended immediately before use or beino ready-to-use together with a pharmaceutically acceptable vehicle; an example of the ready-to-use form is an injectable ampoule.

In therapy employing sustained treatment, pills or capsules can be the suitable form of pharmaceutical preparation because of the long-lasting effects obtained when the medicament is administered orally.

The examples which follow illustrate the invention.

EXAMPLE 1

Preparation of para-(methoxyphenylacetyl)-dehydroalanine 4.95 g ($3 \times 10^{-2}$ mol) of para-(methoxyphenyl)-acetamide are introduced, at ambient temperature, into a 250 milliliters glass flask equipped with a water separator. 3.2 g ($3.6 \times 10^{-2}$ mol) of freshly distilled pyruvic acid and 120 milliliters of benzene are then added. This mixture is then heated to the reflux temperature; when refluxing starts, the solution becomes clear, and then clouds gradually due to the precipitation of the para-(methoxyphenylacetyl)-dehydroalanine. Refluxing is continued until water no longer separates out, this requiring about 48 hours, after which the benzene is stripped off in vacuo.

The para-(methoxyphenylacetyl)-dehydroalanine is extracted by means of a saturated $NaHCO_3$ solution, and 1.7 g of unreacted para-(methoxyphenyl)-acetamide are then filtered off.

When the filtration is complete, a few milliliters of hydrochloric acid are added dropwise until a pH of about 3 or 4 is obtained. The para-(methoxyphenylacetyl)dehydroalanine precipitates and is recovered by filtration and recrystallisation from ethanol. 4.45 g of para-(methoxyphenylacetyl)-dehydroalanine are obtained, in a yield of 62%. The melting point of the product obtained is found to be 186° C. The infra-red spectrum (KBr) reveals absorption bands at 3400 $cm^{-1}$ (—OH), 1700 $cm^{-1}$ (C=O), 1620 $cm^{-1}$ (C=C), 1510 $cm^{-1}$, 1420 $cm^{-1}$ and 1300 $cm^{-1}$. Mass spectrography reveals a peak at 235.

The nuclear magnetic resonance spectrum of para-(methoxyphenylacetyl)-dehydroalanine, dissolved in dimethyl sulphoxide, shows the following chemical shifts, the values being given in $\delta$ (ppm): 1H s 8.96; 2H m 7.20; 2H m 6.86; 1H s 6.32; 1H s 5.69; 3H s 3.73; 2H s 3.61.

EXAMPLE 2

Pharmaceutical composition

A pharmaceutical composition is prepared by mixing 4 g of para-(methoxyphenylacetyl)-dehydroalanine obtained according to Example 1 and 3.2 g of cyclophosphamide.

One million "Taper Liver Tumor" cancer cells are injected intraperitoneally into a group of 10 mice each weighing about 30 g. 48 hours after this injection, the pharmaceutical composition described above is administered again intraperitoneally, in an amount of 180 mg per kg of mouse.

By way of comparison, a group of 10 similar mice to which likewise one million "Taper Liver Tumor" cancer cells have been administered is subjected solely to administration of cyclophosphamide, by intraperitoneal injection, 48 hours after administration of the cancer cells, and a group of 10 other similar mice, to which, again, one million "Taper Liver Tumor" cancer cells have been administered is not subjected to any further treatment whatsoever.

Amongst the group of mice not subjected to any further treatment whatsoever, all die between the eighteenth and the twenty-third day.

Amongst the group of mice only treated with cyclophosphamide, all die between the twenty-second day and the twenty-fifth day.

Amongst the group of mice treated with the pharmaceutical composition according to the invention the mice only die beteen the twenty-eighth and thirty-ninth day.

The treatment of the ascites with the pharmaceutical composition according to the invention thus allows the life of the affected mice to be extended substantially.

EXAMPLE 3

Pharmaceutical compositions containing cyclophosphamide and para-(methoxyphenylacetyl)-dehydroalanine: variation of the amount of para-(methoxyphenylacetyl)dehydroalanine introduced One million "Taper Liver Tumor" cancer cells are injected intraperitoneally into groups of twelve adult male mice, NMRI strain, the mice having a body weight of about 30 grams. 48 hours after this injection various pharmaceutical compositions according to the invention are administered, again intraperitoneally, to the mice, the amount of para-(methoxyphenylacetyl)-dehydroalanine present in the composition administered being varied, and compositions only containing cyclophosphamide also beino administered.

Thereafter, three parameters are measured:

(a) the variations of the mean weight of the mice on the fifth day after inoculation of the cancer tumour (V.M.W.)

(b) the median survival of 12 mice treated with a pharmaceutical composition according to the invention or treated with cyclophosphamide alone (M.S.)

(c) the prolongation of survival of the mice treated with a composition according to the invention relative to comparison mice treated with cyclophosphamide alone (P.S.).

The results obtained are listed in the table below, the para-(methoxyphenylacetyl)-dehydroalanine being referred to by the code S 86. The results reveal a prolongation of survival of the mice if a pharaceutical composition containing doses of 25, 50 or 100 mg/kg of S 86 is administered; the lethal dose ($LD_{50}$) of S 86 is greater than 400 mg per kg of bodyweight in the mouse, this value being the maximum which can be injected into the mouse because of the low solubility of the product.

TABLE I

| Pharmaceutical composition and dose administered | | V.M.W. | M.S. (day) | P.S. (%) |
|---|---|---|---|---|
| Cyclophosphamide | 80 mg/kg | −1 | 24 | |
| Cyclophosphamide + S 86 | 80 mg/kg 400 mg/kg | −7.8 | 18 | −25 |
| Cyclophosphamide + S 86 | 80 mg/kg 200 mg/kg | −5 | 24 | 0 |
| Cyclophosphamide + S 86 | 80 mg/kg 100 mg/kg | −3 | 26 | +15 |
| Cyclophosphamide + S 86 | 80 mg/kg 50 mg/kg | −2 | 27.5 | +15 |
| Cyclophosphamide + S 86 | 80 mg/kg 25 mg/kg | −4 | 26 | +9 |

EXAMPLE 4

Pharmaceutical compositions containing cyclophosphamide and para-(methoxyphenylacetyl)-dehydroalanine: variation of the amount of cyclophosphamide introduced One million "Taper Liver Tumor" cancer cells are injected intraperitoneally into groups of twelve adult male mice, NMRI strain, the mice having a body weight of about 30 grams. 48 hours after this injection various pharmaceutical compositions according to the invention are administered, again intraperitoneally, to the mice, the amount of cyclophosphamide present in the composition administered being varied, and compositions only containing cyclophosphamide also being administered.

Thereafter, three parameters are measured:

(a) the variation of the mean weight of the mice on the fifth day after inoculation of the cancer tumour (V.M.W.)

(b) the median survival of 12 mice treated with a pharmaceutical composition according to the invention or treated with cyclophosphamide alone (M.S.)

(c) the prolongation of survival of the mice treated with a composition according to the invention relative to comparison mice treated with the same dose of cyclophosphamide (P.S).

The results obtained are listed in the table below, the para-(methoxyphenylacetyl)-dehydroalanine being referred to by the code S 86. They show a marked prolongation of the survival time when pharmaceutical compositions according to the invention containing doses of cyclophosphamide equal to or greater than 360 mg/kg are administered. It is also noticeable that the mean weight of the mice varies less in the case of the mice treated with pharmaceutical compositions according to the invention than in the case of the mice treated with cyclophosphamide.

TABLE II

| Pharmaceutical composition and dose administered | | V.M.W. | M.S. (day) | P.S. (%) |
| --- | --- | --- | --- | --- |
| Cyclophosphamide | 80 mg/kg | −2.2 | 21 | |
| Cyclophosphamide + S 86 | 80 mg/kg 50 mg/kg | −2.6 | 22 | +5 |
| Cyclophosphamide | 180 mg/kg | −4.4 | 23 | |
| Cyclophosphamide + S 86 | 180 mg/kg 50 mg/kg | −3 | 18.5 | −17 |
| Cyclophosphamide | 360 mg/kg | −6.6 | 31 | |
| Cyclophosphamide + S 86 | 360 mg/kg 50 mg/kg | −10 | 34 | +10 |
| Cyclophosphamide | 450 mg/kg | −14 | 20 | |
| Cyclophosphamide + S 86 | 450 mg/kg 50 mg/kg | −10.4 | 34 | +70 |
| Cyclophosphamide | 540 mg/kg | −18.6 | 12 | |
| Cyclophosphamide + S 86 | 540 mg/kg 50 mg/kg | −11.6 | 38.5 | +204 |

EXAMPLE 5

Inhibition of the toxicity of doxorubicin in vivo

Subcutaneous injection of a single dose of doxorubicin (10 mg/kg) to rats causes, in the liver, a reduction of 20% in the minimum content of cytochrome P450, a drop in benzo(a)pyrene hydroxylase activity and a reduction of 85% in the aldrin mono-oxygenase activity. The administration of cysteamine, used as a reference antitoxic substance, does not protect against the effect of doxorubicin on the level of cytochrome P450. On the other hand the drop in benzo(a)pyrene hydroxylase activity is no more than 20% and the decrease in aldrin mono-oxygenase activity is reduced to 40%.

A single dose (10 mg/kg) of a composition containing equal amounts by weight of doxorubicin and of para-(methoxyphenylacetyl)-dehydroalanine was injected into rats. A 60% increase in the minimum content of cytochrome P450, a 20% increase in the benzo(a)pyrene hydroxylase activity and a 5% decrease in the aldrin mono-oxygenase activity were observed.

It emerges from these tests that the acylated enamide compound according to the invention completely protects against the abovementioned three toxic effects of doxorubicin.

EXAMPLE 6

Pharmaceutical composition

A pharmaceutical composition is prepared by mixing 4 g of para-(methoxyphenylacetyl)-dehydroalanine obtained according to Example 1 and 0.2 g of doxorubicin.

One million L311 leukaemia cells are injected intraperitoneally into a group of six rats, LOU/2 strain, the mean body weight of the rats being 160 g. L311 leukaemia is a tumour transplantable in rats of strain LOU/2, the tumour being described in the article by C. Deckers, F. Mare, L. Deckers-Passeu and A. Trouet, Adriamycin Review, Part I, 1973, pages 79 to 86.

48 hours after this injection the pharmaceutical composition described above is administered to the rats, again intraperitoneally, in an amount of 105 mg per kg of rat.

By way of comparison, a group of twelve similar rats to which one million L311 leukaemia cells have also been administered is subjected solely to intraperitoneal administration of doxorubicin 48 hours after the administration of the L311 leukaemia cells, and a group of twelve similar rats to which one million L311 leukaemia cells have also been administered is given no subsequent treatment whatsoever.

The mean length of survival after administration of the leukaemia cells is 15.9 days in the case of the untreated leukaemic rats, 27.6 days for those treated solely with doxorubicin and 33.6 days for the rats treated with the composition according to the invention.

For the untreated leukaemic rats, the first death occurs fourteen days after administration of the leukaemia cells. The corresponding figure is sixteen days for the rats treated with doxorubicin and twenty-one days for the rats treated with the composition according to the invention.

The treatment of leukaemia with the compositions according to the invention thus permits a substantial prolongation of life of the leukaemic rats.

EXAMPLES 7 TO 11

Following a method similar to that described in Example 1, the compounds of the general formula (I) in which n=1 and Z has the meaning indicated below were prepared.

| Example No. | Z | Yield (%) | Melting point (°C.) |
| --- | --- | --- | --- |
| 7 | —OC$_2$H$_5$ | 41 | 142 |
| 8 | —OCH$_2$—C$_6$H$_5$ | 62 | 188 |
| 9 | —OCH$_2$—CH$_2$—CH$_3$ | 30 | 178 |
| 10 | —OCH(CH$_3$)$_2$ | 18 | 173 |
| 11 | —SCH$_3$ | 71 | 209 |

These compounds exhibit a detoxifying effect similar to that of the compound of Example 1.

EXAMPLE 12

Preparation of sodium α-(para-methoxyphenyl)acetamido-acrylate[sodium N-(para-methoxyphenylacetyl)dehydroalaninate]

2.35 g ($10^{-2}$ mol) of the acid (para-methoxyphenylacetyl-dehydroalanine) are dissolved in 100 ml of methanol containing 0.54 g of sodium methanolate.

Evaporation of the solvent gives a white solid.

Recrystallisation from isopropanol gives 2.25 g (87%) of the sodium salt.

Melting point: 112° C. (polymerisation).

NMR (D$_2$O)δ (ppm): 7.0–6.5(4H, m) 5.7(1H, s) 5.4(1H, s) 4.5(H$_2$O) 3.5(3H, s) 3.3(2H, s).

We claim:

1. Acylated enamide compounds, characterised in that they are compounds corresponding to the general formula

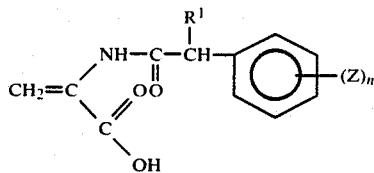

in which
- Z represents an electron donor group selected from the electron donor groups comprising a halogen or a chemical group selected from the groups comprising $OR^2$, $SR^2$, $SeR^2$, $N=R^2$ or $NR^2R^3$, in which the oxygen (O), sulphur (S), selenium (Se) and nitrogen (N) can form part of a ring and $R^2$ and $R^3$ can be identical or different and represent hydrogen or a saturated or unsaturated aliphatic or cyclic organic group containing 1 to 20 carbon atoms;
- n is 1, 2 or 3; and
- $R^1$ represents hydrogen, a halogen, a substituted or unsubstituted aliphatic group containing from 1 to 4 carbon atoms or an aromatic group containing from 5 to 8 carbon atoms;
- or salts, complexes, alkylated derivatives or acylated derivatives of these compounds.

2. Acylated compounds according to claim 1 wherein Z is an $OR^2$ group, where $R^2$ represents hydrogen or a substituted or unsubstituted alkyl group having from 1 to 6 carbon atoms.

3. Acylated enamide compounds according to any one of claims 1, or 2 characterised in that they consist of (methoxyphenylacetyl)-dehydroalanines.

4. Acylated enamide compounds according to any one of claims 1, 2 or 3, used as a medicament.

5. Pharmaceutical compositions consisting essentially of an acylated enamide compound according to any one of claims 1, 2 or 3 and a pharmaceutically acceptable carrier.

6. Pharmaceutical compositions according to claim 5, including an antineoplastic substance selected from the group comprising nitrogen mustard, an antibiotic or anti-pyrimidine compound.

7. Pharmaceutical compositions according to claim 6, wherein the antineoplastic substance is cyclophosphamide, daunorubicin, fluorouracil or doxorubicin.

8. Pharmaceutical compositions according to claim 5 used in the treatment of liver and leukemia cancers.

9. Process for the preparation of acylated enamide compounds according to any one of claims 1, 2 or 3, characterised in that an amide of the formula

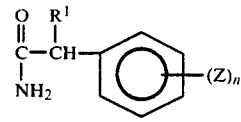

is reacted with pyruvic acid wherein:
- Z represents an electron donor group selected from the electron donor groups comprising a halogen or a chemical group selected from the groups comprising $OR^2$, $SR^2$, $SeR^2$, $N=R^2$ or $NR^2R^3$, in which the oxygen (O), sulphur (S), selenium (Se) and nitrogen (N) can form part of a ring and $R^2$ and $R^3$ can be identical or different and represent hydrogen or a saturated or unsaturated aliphatic or cyclic organic group containing 1 to 20 carbon atoms;
- n is 1, 2 or 3; and
- $R^1$ represents hydrogen, a halogen, a substituted or unsubstituted aliphatic group containing from 1 to 4 carbon atoms or an aromatic group containing from 5 to 8 carbon atoms;
- or salts, complexes, alkylated derivatives or acylated derivatives of these compounds.

10. Pharmaceutical compositions according to claim 6 used in the treatment of liver and leukemia cancers.

11. Pharmaceutical compositions according to claim 7 used in the treatment of liver and leukemia cancers.

* * * * *